US012365644B2

(12) United States Patent
Aramini et al.

(10) Patent No.: US 12,365,644 B2
(45) Date of Patent: Jul. 22, 2025

(54) CO-CRYSTAL OF KETOPROFEN, LYSINE AND GABAPENTIN, PHARMACEUTICAL COMPOSITIONS AND THEIR MEDICAL USE

(71) Applicant: DOMPÉ FARMACEUTICI S.P.A., Milan (IT)

(72) Inventors: Andrea Aramini, L'Aquila (IT); Marcello Allegretti, Rome (IT); Gianluca Bianchini, L'Aquila (IT); Samuele Lillini, Cardito (IT); Mara Tomassetti, Naples (IT)

(73) Assignee: DOMPÈ FARMACEUTICI S.P.A., Milan (IT)

( * ) Notice: Subject to any disclaimer, the term of this patent is extended or adjusted under 35 U.S.C. 154(b) by 485 days.

(21) Appl. No.: 17/922,999

(22) PCT Filed: May 4, 2021

(86) PCT No.: PCT/EP2021/061640
§ 371 (c)(1),
(2) Date: Nov. 3, 2022

(87) PCT Pub. No.: WO2021/224217
PCT Pub. Date: Nov. 11, 2021

(65) Prior Publication Data
US 2023/0357121 A1 Nov. 9, 2023

(30) Foreign Application Priority Data
May 4, 2020 (EP) ..................................... 20172660

(51) Int. Cl.
*C07C 59/84* (2006.01)
*C07C 229/26* (2006.01)
*C07C 229/28* (2006.01)

(52) U.S. Cl.
CPC ............ *C07C 59/84* (2013.01); *C07C 229/26* (2013.01); *C07C 229/28* (2013.01); *C07B 2200/13* (2013.01); *C07C 2601/14* (2017.05)

(58) Field of Classification Search
CPC ..... C07C 59/84; C07C 229/26; C07C 229/28; C07C 2601/14; C07B 2200/13
See application file for complete search history.

(56) References Cited

U.S. PATENT DOCUMENTS

2014/0031403 A1  1/2014  Gately et al.
2023/0181507 A1*  6/2023  Aramini ............... A61K 31/192
                                          514/564

FOREIGN PATENT DOCUMENTS

| EP | 3670489 | 6/2020 |
|----|---------|--------|
| EP | 3842488 | 6/2021 |
| GB | 1497844 | 1/1978 |
| RU | 2564015 | 9/2015 |
| RU | 2599717 | 10/2016 |
| WO | WO 2010/043412 | 4/2010 |
| WO | WO 2012/071517 | 5/2012 |
| WO | WO2017186714 | 6/2017 |
| WO | WO2020126088 | 6/2020 |

OTHER PUBLICATIONS

Deng et al. BMC Anesthesiology (2016) 16:12.
Enteshari-Moghaddam et al, Clinical Rheumatology 2019: 38, 2873-2880.
Low back pain and sciatica in over ios: assessment and management, National Institute for Health and Care Excellence NICE Guidelines 2016.
M. A. Rose, Anaesthesia, 2082, 57, pp. 451-462.
Moore et al, Cochrane Database Syst Rev. Apr. 27, 2014;(4):C0887938.
Quintero, Journal of Experimental Pharmacology 2017:9 13-21.
Ru-Rong Bil Nat. Rev. Drug Discov. Jul. 2014; 13(7): 533-548.
Caira, Topics in Current Chemistry, 1998, vol. 198, 163-208.
Duggirala, et al., Chem. Commun., 2016, 52, 640-655.
English Abstract for RU 2564105. Sep. 27, 2015.
Morissette, et al., Advanced Drug Delivery Reviews, 2004, 56, 275-300.
Rodriguez-Spong, et al., Advanced Drug Delivery Reviews, 2004, 56, 241-274.
Sarma, et al., Korean J. Chem. Eng., 2011, 28(2), 315-322.
Yadav, et al., Indian Journal of Pharmaceutical Science, Jul.-Aug. 2009, 71, 359-370.
International Search Report for PCT/EP2021/061648 dated Jul. 1, 2022.
Almansa, et al., Journal of Pain Research. 2019, 12, 2679-2689.
Wenger, et al., Crystal Growth & Design, 2008, 8, 1595-1598.

* cited by examiner

*Primary Examiner* — Matthew P Coughlin
(74) *Attorney, Agent, or Firm* — HUESCHEN AND SAGE (57) ABSTRACT

The present invention relates to a new co-crystal of Ketoprofen, Lysine and Gabapentin, to pharmaceutical compositions and to their use in the prevention, reduction or treatment of pain and/or inflammation.

18 Claims, 8 Drawing Sheets

CO-CRYSTAL OF KETOPROFEN, LYSINE AND GABAPENTIN, PHARMACEUTICAL COMPOSITIONS AND THEIR MEDICAL USE

The present invention relates to a co-crystal of Ketoprofen, Lysine and Gabapentin, to a process for its preparation, to a pharmaceutical composition comprising said co-crystal and to the use of said co-crystal or pharmaceutical composition in the treatment of acute or chronic pain, in particular in the treatment of neuropathic or inflammatory pain.

BACKGROUND ART

Pain is a sensory and emotional experience usually arising from actual or potential tissue damage. Pain conditions can be divided in acute and chronic.

Acute pain is a pain that lasts for a short period, typically less than 3 months, and is commonly associated with tissue injury, inflammation, a surgical procedure, childbirth, or a brief disease process.

Chronic pain has been recognized as a pain that persists past normal healing time and hence lacks the acute warning function of physiological nociception. Usually pain is classified as chronic when it lasts or recurs for more than 3 months.

Chronic pain may have different etiologies and includes neuropathic pain, chronic inflammatory pain, for example arthritis, or pain of unknown origin, as fibromyalgia and restless leg syndrome.

Chronic neuropathic pain is caused by a lesion or disease of the somatosensory nervous system that provides information about the body including skin, musculoskeletal, and visceral organs, A number of diseases or pathological conditions can cause a damage to the sensory neurons resulting in hyperalgesia or allodynia, such for example in lower back pain, sciatalgia, post-operative pain, cancer pain, phantom limb pain, HIV pain, diabetic neuropathy pain, Herpes Zoster pain or trigeminal neuralgia.

Chronic inflammatory pain is associated to strong inflammation of infectious, autoimmune or metabolic etiology, such as rheumatoid arthritis, and by structural changes affecting bones, joints, tendons, or muscles, such as osteoarthrosis. Therapy of this type of pain usually includes the use of non-steroidal anti-inflammatory drugs, acetaminophen, and other disease-modifying agents.

Because of its complex etiology, the pharmacological treatment of neuropathic pain differs from the treatment of non-neuropathic pain. Guidelines recommend the use of serotonin and norepinephrine reuptake inhibitors, tricyclic antidepressants, anticonvulsants, or topical lidocaine treatment as first-line and second-line medications for the management of neuropathic pain, with opioids usually recommended as second- or third-line therapies (Deng et al. BMC Anesthesiology (2016) 16:12). Acetaminophen and non-steroidal anti-inflammatory drugs are largely ineffective in neuropathic pain.

Neuroinflammation is a physiological/pathological condition characterized by infiltration of immune cells, activation of glial cells and production of inflammatory mediators in the peripheral and central nervous system.

Recent progress indicates that the development of neuroinflammation of tissue, within the peripheral nervous system (PNS) and central nervous system (CNS), is responsible for generating and sustaining the sensitization of nociceptive neurons leading to chronic pain. Neuroinflammation occurs in the PNS (that is, peripheral nerves and ganglia) and CNS (that is, spinal cord and brain) and is characterized by infiltration of leukocytes and increased production of inflammatory mediators at these sites. The trafficking of different types of leukocytes in the PNS and CNS occurs with different temporal profiles. Neuroinflammation manifests as activation of glial cells, such as Schwann cells in the nerve, satellite glial cells in the ganglia and microglia, and astrocytes and oligodendrocytes in the spinal cord and brain. Activation of glial cells leads to the production of glial mediators that can modulate pain sensitivity.

Neuroinflammation is a local inflammation, which means that it is more effective at eliciting and sustaining pain than systemic inflammation, yet it is difficult to detect in clinic. For example, fibromyalgia, a chronic muscle pain condition, was previously regarded as an atypical pain, because no obvious pathologies and inflammation could be detected in affected patients. However, a recent study identified neuropathy of small nerve fibres in patients with fibromyalgia, which could be a result and also a cause of chronic neuroinflammation. Neuroinflammation appears to be permanent in patients with chronic pain but also occurs in non-chronic conditions such as for example post-surgical pain.

The lack of efficacy of currently available therapies in the management of neuroinflammatory conditions call for the identification of novel specific and safe drugs for the treatment of still unmet medical needs associated with acute or chronic neuro-inflammatory processes (Ru-Rang Jil. Nat. Rev. Drug Discov. 2014 July; 13(7): 533-548.

Gabapentin is an anticonvulsant synthetic analogue of the neurotransmitter gamma-aminobutyric acid (GABA) of formula (I)

Although its exact mechanism of action is unknown, gabapentin appears to inhibit excitatory neuron activity. The molecule was originally developed as a chemical analogue of gamma-aminobutyric acid to reduce the spinal reflex for the treatment of spasticity but it was found to have no activity on the GABAergic system. Its mechanism of action includes binding to calcium channels in several areas of the central nervous system and spinal cord in which these channels are expressed. Calcium channels are localized on presynaptic terminals, where they control neurotransmitter release.

Gabapentin was approved for use as an adjunct treatment for partial epileptic seizures in adults and children in 1993. More recently; Gabapentin has also been approved for the treatment of chronic pain, in particular neuropathic pain syndromes. It was also claimed to be beneficial in several other clinical disorders such as anxiety, bipolar disorder, and hot flashes. Gabapentin was also proven effective at high dosage in the treatment of fibromyalgia (Moore et al, Cochrane Database Syst Rev. 2014 Apr. 27; (4):CD007938; Deng et al., BMC Anesthesiology (2016) 16:12).

However, a number of studies have demonstrated an unsatisfactory pharmacological and pharmacokinetic profile when Gabapentin is used alone in pain therapy, for instance in terms of scarce efficacy on specific types of pain, side effects or delayed onset of the response. In fact, Gabapentin is absorbed slowly after oral administration, and it has an utmost level in plasma within 3-4 hours (Quintero, Journal of Experimental Pharmacology 2017:9 13-21).

The plasma level of gabapentin does not increase proportionally if its dosages are increased, thus requiring careful titration on individual basis at the start of a treatment; gabapentin does not attach to plasma proteins.

Gabapentin is neither inhibited nor metabolized by hepatic enzymes; besides, gabapentin can be expelled by the renal system, and its excretion half-life is roughly 6 hours. The most common side effects of gabapentin are somnolence (20%), dizziness (18%), ataxia (13%) and fatigue (11%).

Oral doses of gabapentin are administered three times a day (tds) because of its short half-life. Rapid titration may be achieved with doses of 300 mg once daily (often at bedtime to minimize sedation) on the first day followed by 300 mg twice daily on the second day and 300 mg tds on the third day. Dosage may be further increased if efficacy is not achieved at this dose.

The recommended starting dose in the treatment of neuropathic pain is 300 mg three times a day with titration if necessary to a maximum of 3600 mg·day-1 but doses up to 4200 mg, have been reported when limited or no efficacy is observed (M. A. Rose, Anaesthesia, 2002, 57, pages 451-462).

For example, Gabapentin is not recommended for the treatment of lower back pain because it demonstrates little efficacy together with increased risk of side effects (*Low back pain and sciatica in over 16 s: assessment and management*, National Institute for Health and Care Excellence NICE Guidelines 2016).

Furthermore, Gabapentin is little active on inflammatory pain.

It was also shown that the therapeutic effect of Gabapentin in the treatment of osteoarthritis starts only after a prolonged administration of 3 months (Enteshari-Moghaddam et al, Clinical Rheumatology 2019: 38, 2873-2880).

The Applicant has undertaken studies to improve the properties of Gabapentin, with the aim of improving the activity of the molecule on pain conditions and extending the efficacy to other pain syndromes and possibly reducing dose related side effects.

In particular, the Applicant has carried out investigations on Gabapentin combined with Ketoprofen, specifically with Ketoprofen Lysine.

Ketoprofen, (RS)-2-(3-benzoylphenyl)-propionic acid, is a well-established nonsteroidal anti-inflammatory drug (NSAID) with analgesic and antipyretic effects of formula II (II)

Because of its high tolerability, Ketoprofen is one of the non-steroidal anti-inflammatory drugs of widespread use in clinics, both for the treatment of serious inflammatory conditions and for its use in analgesic and antipyretic by inhibiting the body's production of prostaglandin.

Pharmaceutical compositions of current use containing Ketoprofen have as active ingredient the racemate, where the two enantiomers S(+) and R(−) are present in equimolecular ratio.

Current Ketoprofen pharmaceutical compositions for oral use may contain the active ingredient as free acid, which, however, shows a very low solubility in water and therefore a low bioavailability.

In order to improve dissolution profile and bioavailability of the active ingredient, salts of Ketoprofen are also advantageously used.

These salts are used for example in the treatment by oral administration of those pathological symptoms of rheumatoid and chronic type, which require the drug to be administered at high dosage, continuously and for long period of time and in pain manifestation that require an immediate analgesic effect.

In particular, the salt of Ketoprofen with the aminoacid Lysine, although presenting a parallel pharmaceutical profile and a similar anti-inflammatory-analgesic potency compared to the free acid, offers the advantage of a considerably higher solubility in water that enables rapid and almost complete absorption of the compound ensuring a rapid onset of action and a greater gastric tolerability.

Ketoprofen is generally prescribed for arthritis-related inflammatory pains, severe toothaches, treatment of musculoskeletal pain, neuropathic pain such as sciatica, post herpetic neuralgia and referred pain for radiculopathy.

Ketoprofen mechanism of action is essentially based on the inhibition of the biosynthesis of prostaglandins, prostacyclins and thromboxane.

Depending on process conditions, Ketoprofen and Lysine can combine forming either a salt or co-crystals having different crystalline forms (polymorphs) as described in the European Patent Applications n. EP18215336.1 and EP19219293.8 and in the International Patent Application PCT/EP2019/025464.

SUMMARY OF THE INVENTION

The Applicant during these investigations has unexpectedly found that Ketoprofen and Lysine form a new stable co-crystal with Gabapentin, in a molar ratio of 1:1:2.

It is thus an object of the present invention a co-crystal of Ketoprofen, Lysine and Gabapentin wherein the molar ratio of the components is 1:1:2.

The co-crystal is characterized by the following XRPD diffraction peaks: 3.6, 6.3, 18.6 and 21.7 degrees 2-theta±0.2 degrees 2-theta, preferably further characterized by the following XRPD diffraction peaks: 9.6, 17.2 and 20.5 degrees 2-theta±0.2 degrees 2-theta.

A further object of the present invention is a process for the preparation of the co-crystal of the invention, which comprises:
a) suspending Ketoprofen, Lysine and Gabapentin, in a molar ratio of 1/1 to 1.5/2 to 2.5, in a suitable solvent.
b) dissolving Ketoprofen, Lysine and Gabapentin, optionally by heating the is suspension and/or under stirring, till a clear solution is obtained
c) subsequently cooling the solution, and
d) optionally adding an anti-solvent.

A further object of the present invention is a pharmaceutical composition comprising the co-crystal of the invention and at least a pharmaceutically acceptable excipient.

A further object of the present invention is a pharmaceutical composition composing the co-crystal of the invention and at least another pharmaceutically active ingredient.

A further object the present invention is the co-crystal of the invention for use as a medicament.

A further object of the present invention is the co-crystal of the invention for use in the treatment of pain and/or inflammation.

A further object of the present invention is a method for the treatment of pain and/or inflammation comprising administering to the patient an effective amount of the co-crystal of the invention.

Definitions

For the purpose of the present invention, the term "pharmaceutically acceptable excipient" refers to a substance devoid of any pharmacological effect of its own and which does not produce adverse reactions when administered to a mammal, preferably a human.

For the purpose of the present invention, the term "room temperature" means a temperature range of 18 to 25° C.

For the purpose of the present invention, the term "co-crystal" means a multi-component system, in which all components are solid under ambient conditions when in their pure form. The components coexist at a molecular level within a single crystal. At least some the components are connected by non-covalent, non-ionic interactions.

For the purpose of the present invention, the term "pain" means pain caused by disturbances of different nature and origin, such as, for example: headache or cephalalgia: both primary and therefore not related to other factors or diseases, and secondary and therefore dependent on trauma, injury and distinct diseases; toothache: in case of abscesses or caries that create pain in the dental pulp, with numerous blood vessels and nerves; menstrual pains: abdominal and lower abdominal pain and headaches caused by hormonal changes typical of the period is of menstruation; neuralgia, or intense nerve pain due to strains, trauma and infections; pain in the muscles, or myalgia: pains located at the level of muscles when using or touching them, due to sudden contractions or traumas; osteoarticular pains, such as joint inflammations (to the bones, cartilages, ligaments and tendons) following traumas, old age, strains and injuries.

For the purpose of the present invention, the term "inflammation" means the local response of an organism to cellular injury that is marked by capillary dilatation, leukocytic infiltration, redness, heat, and pain and that serves as a mechanism initiating the elimination of noxious agents and of damaged tissue.

For the purpose of the present invention, the term "antisolvent" mean a solvent in which a compound is insoluble or little soluble.

The terms "approximately" and "about" herein refers to the range of the experimental error, which may occur in a measurement.

BRIEF DESCRIPTION OF THE FIGURES

Keys in the Figures: K-L-GAB Co-xx Ketoprofen Lysine Gabapentin co-crystal.

DETAILED DESCRIPTION OF THE INVENTION

An object of the present invention is a co-crystal of Ketoprofen, Lysine and Gabapentin wherein the molar ratio of the components is 1:1:2.

In line with the solid state $^{13}$C-NMR analysis reported in the experimental part, in the present co-crystal Ketoprofen carboxylic group is deprotonated and interacts with protonated Lysine ε-$NH_3^+$ group through ionic bonds forming a neutral salt. The Ketoprofen Lysine neutral salt interacts with two molecules of Gabapentin through non-ionic bonds.

Figure 1:
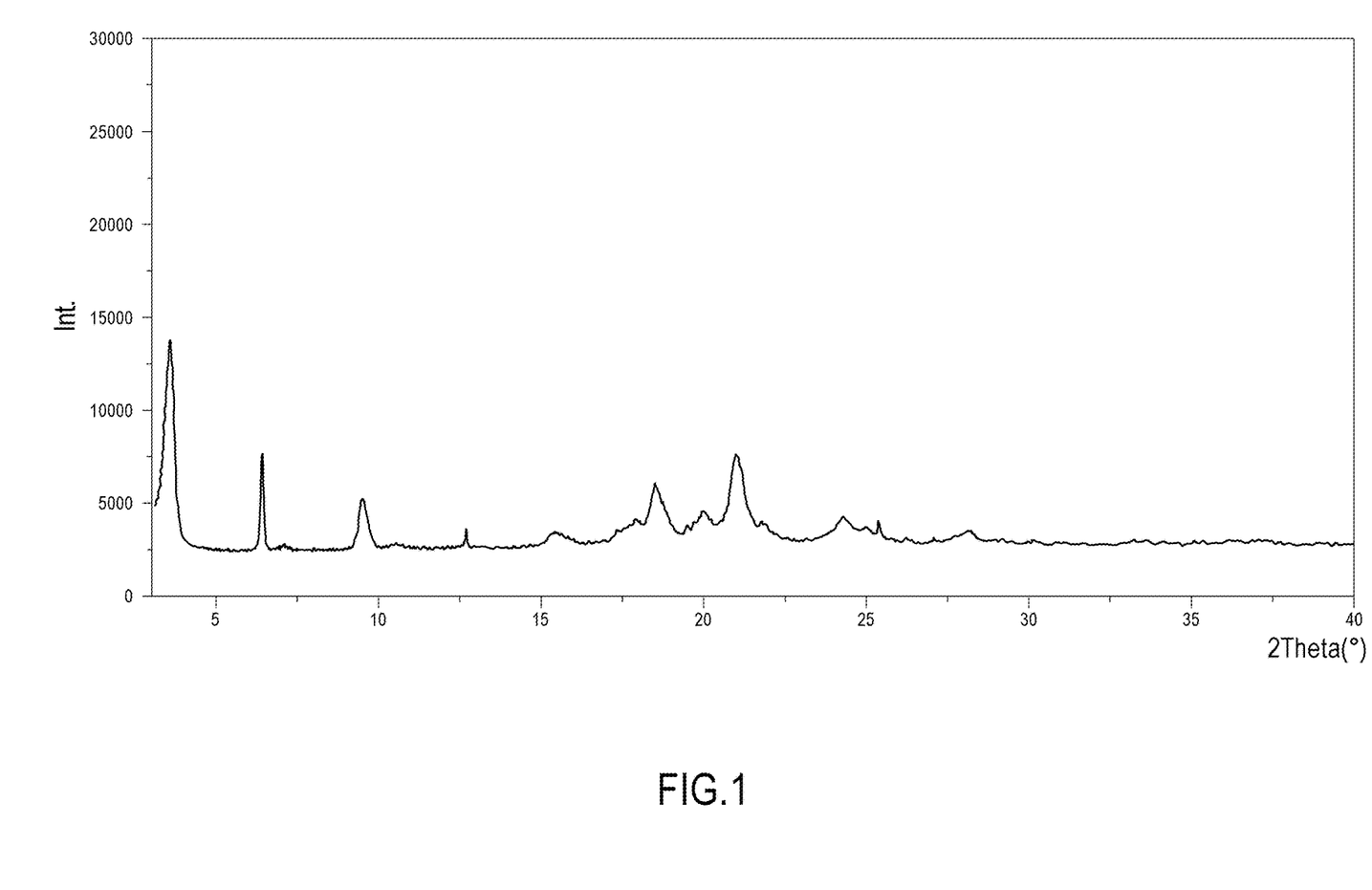
FIG. 1: Powder X-Ray diffraction pattern of 1:1:2 Ketoprofen-Lysine-Gabapentin co-crystal

The co-crystal of the present invention is further characterized by the following XRPD diffraction peaks: 3.6, 6.3, 18.6 and 21.7 degrees 2-theta±0.2 degrees 2-theta, with a margin of error on the value indicated for each peak of ±0.2 degrees 2-theta, preferably further characterized by the following XRPD diffraction peaks: 9.6, 17.2 and 20.5 degrees 2-theta±0.2 degrees 2-theta, as shown in FIG. 1 and in Table 2.

This crystalline form of the co-crystal of the invention is herein named Form I.

Other polymorphs of the present co-crystal are also within the scope of the invention.

Figure 3:
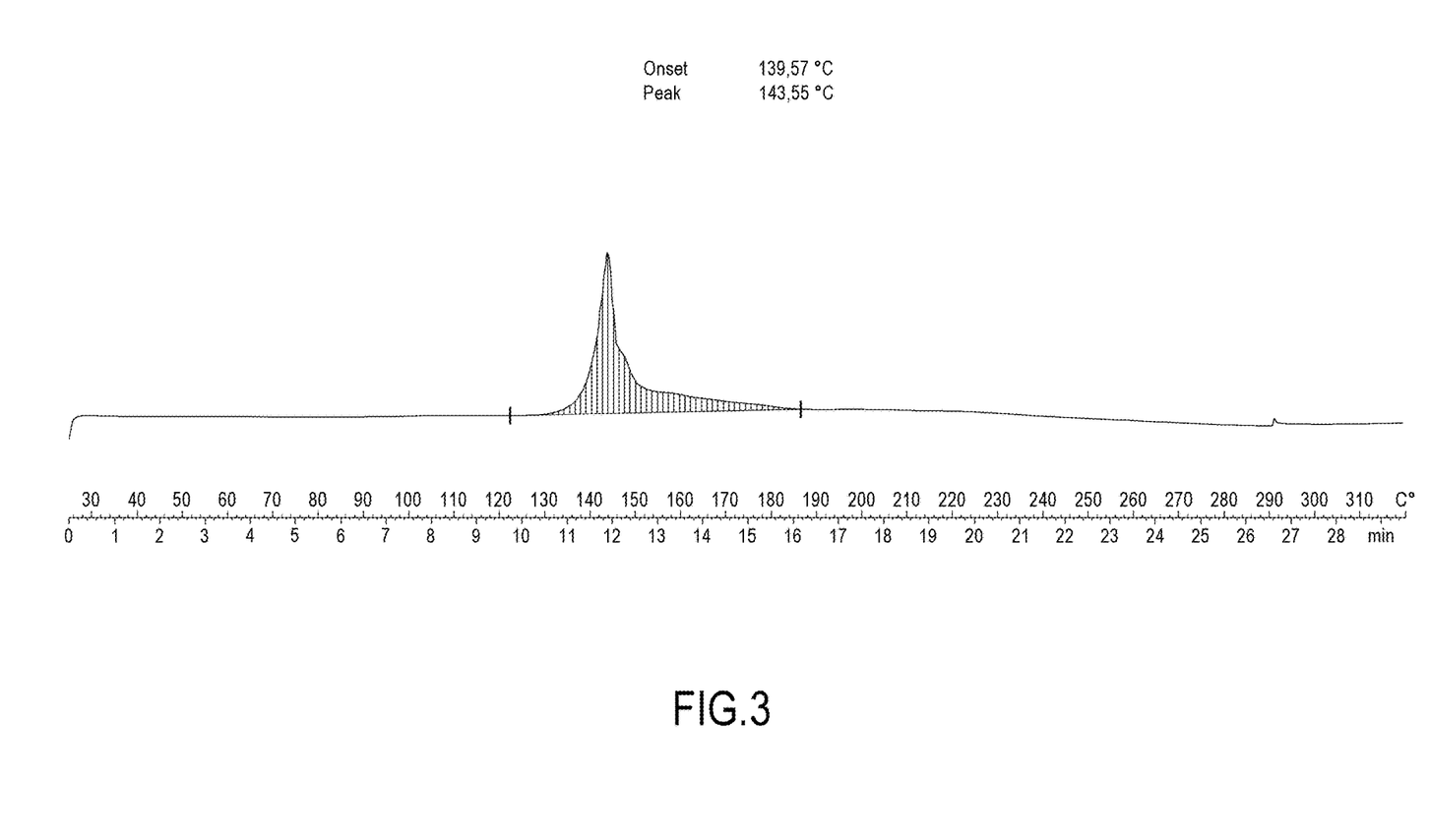
FIG. 3: DSC thermogram of 1:1:2 Ketoprofen-Lysine-Gabapentin co-crystal
Figure 7:
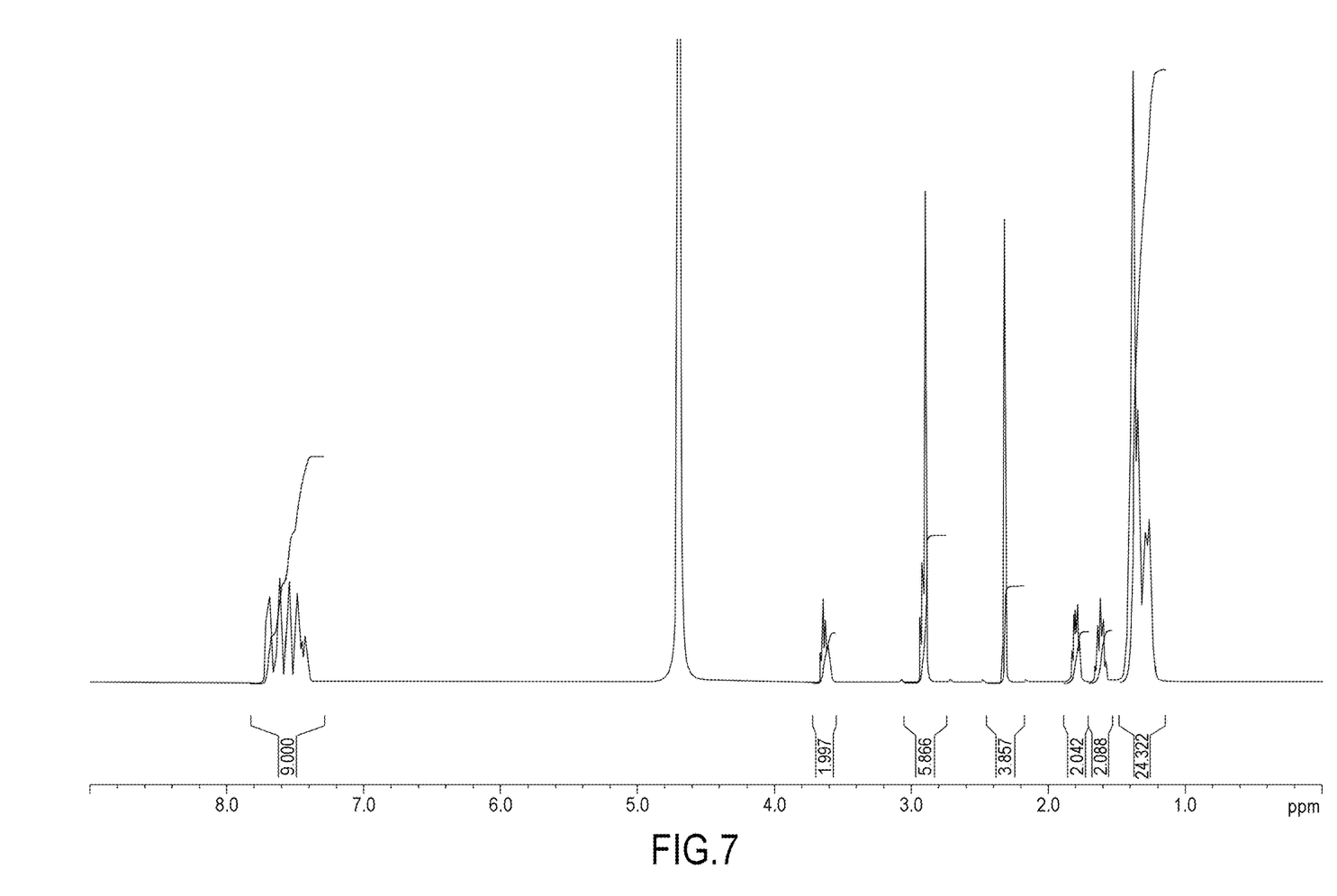
FIG. 7: $^1$H-NMR spectrum (400 MHz, $D_2O$) of 1:1:2 Ketoprofen-Lysine-Gabapentin co-crystal.
Figure 8:
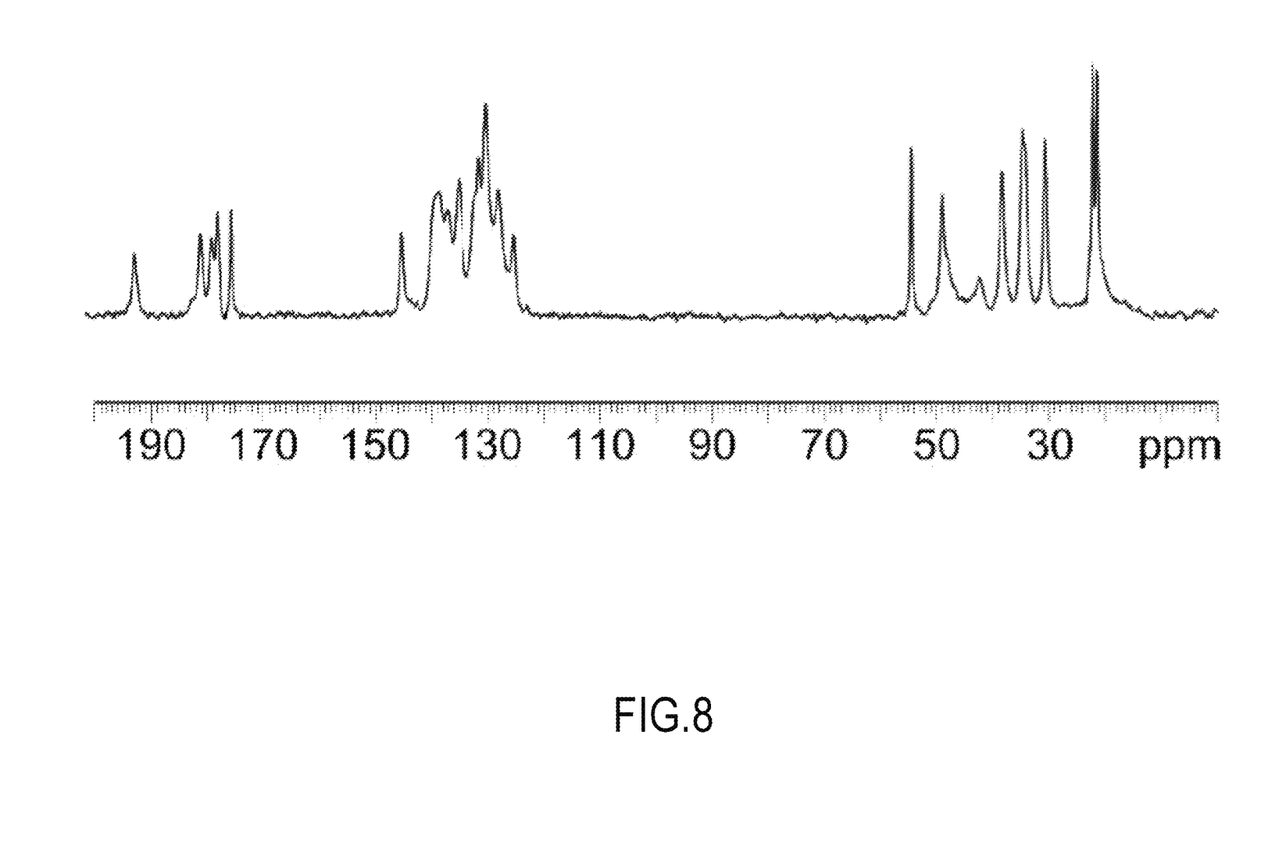
FIG. 8: $^{13}$C-CPMAS ss-NMR of 1:1:2 Ketoprofen-Lysine-Gabapentin co-crystal.

The co-crystal of the present invention is further characterized by the DSC thermogram of FIG. 3, with the endothermic sharp peak of the co-crystal corresponding to the melting point at 143.5° C. with an onset at 139.6° C., by solution $^1$H-NMR spectrum of FIG. 7 and relative assignments in Table 4 and solid state $^{13}$C CPMAS of FIG. 8 and relative assignments in Table 5.

In the co-crystal of the invention, Ketoprofen can be racemic (S,R) Ketoprofen, (S)-Ketoprofen or (R)-Ketoprofen or any admixture thereof.

In one embodiment Ketoprofen is (S)-Ketoprofen (also named DexKetoprofen).

In another embodiment Ketoprofen is (R)-Ketoprofen.

In the co-crystal of the invention, Lysine can be racemic (S,R) Lysine, (S) Lysine or (R) Lysine, or any admixture thereof, preferably is the natural aminoacid (S)-Lysine also named L-Lysine.

In one embodiment, the co-crystal of the invention comprises (S)-Ketoprofen.

In one embodiment, the co-crystal of the invention comprises (S)-Lysine.

In one embodiment, the co-crystal of the invention comprises (S)-Ketoprofen and (S)-Lysine.

The co-crystal of the present invention can exist in unsolvated forms as well solvated forms, including hydrated forms.

The co-crystal of the present invention is easily obtainable and stable.

The co-crystal of the present invention can show improved pharmaceutical properties, pharmacokinetics and efficacy in pain conditions, especially when compared to Gabapentin or Ketoprofen alone and even when compared to their admixture.

A further object of the present invention is a process for the preparation of the co-crystal of the invention, which comprises:
a) suspending Ketoprofen, Lysine and Gabapentin, in a molar ratio of 1/1 to 1.5/2 to 2.5, in a suitable solvent,
b) dissolving Ketoprofen, Lysine and Gabapentin, optionally by heating the suspension and/or under stirring, till a clear solution is obtained
c) subsequently cooling the solution, and
d) optionally adding an anti-solvent.

In the present process, the starting material for Ketoprofen can be Ketoprofen free acid or a Ketoprofen salt, preferably Ketoprofen Lysinate, or any Ketoprofen Lysine co-crystal. In case of Ketoprofen free add or a Ketoprofen salt different from the Lysinate, Lysine is added, preferably in its neutral form. Lysine is preferably used in the same molar amount of Ketoprofen.

Ketoprofen and Lysine can be in any optical form, namely as any pure optical Isomer or in any admixture of optical isomers, including racemates.

In step a) of the present process, the molar ratio of Gabapentin vs Ketoprofen is preferably between 2:1 and 2.5:1, more preferably between 2:1 and 2.2:1, even more preferably is about 2:1.

In one embodiment, the molar ratio of Ketoprofen Lysine Gabapentin in step a) is about 1:1:2.

In the present process, suitable solvents are alcohols, preferably methanol and ethanol, esters, preferably ethyl acetate, ethers, preferably tetrahydrofuran and tert-butylmethyl ether or aromatic solvents, preferably toluene.

Preferably, step b) is performed under heating at the temperature of reflux of the solvent.

Preferably, the solution from step b) is cooled at room temperature.

Preferably the solution from step b) is cooled at room temperature and filtered

Preferably, the precipitation of the co-crystal is favored by addition of an anti-solvent.

The present process provides the co-crystal of the invention with high yields. It is simple and easy scalable at industrial level.

According to one embodiment, in step a) of the process according to the invention, Ketoprofen and Lysine may be present as a pre-formed salt or co-crystal, in any polymorphic form.

The starting material for the manufacture of the co-crystal of the present invention is Gabapentin, Ketoprofen and Ketoprofen Lysine salt or co-crystals may be prepared in accordance with methods of synthesis previously published and well known to the organic chemist of ordinary skill.

Ketoprofen Lysine salt can be prepared as described for instance in GB1497044A and BE882889.

Ketoprofen Lysine co-crystal Form I can be prepared as described for instance in the European Patent Application n. EP18215336.1 or in the International Patent Application PCT/IEP2019/025464.

Ketoprofen Lysine co-crystal Form IV can be prepared as described for instance n EP19219293.8.

According to an alternative embodiment, said Ketoprofen is a free acid and/or said Lysine is in neutral form.

In the present preparation process, Gabapentin is preferably used in its neutral form (zwitterionic internal salt) or in any acid or basic salified form, for instance as Gabapentin hydrochloride or Gabapentin Sodium salt.

Preferably, Gabapentin is used in its neutral form.

Gabapentin can be in any polymorph form.

The present invention furthermore relates to a pharmaceutical composition comprising the co-crystal of Ketoprofen-Lysine-Gabapentin according to the present invention, in particular the co-crystal of Ketoprofen-Lysine-Gabapentin as defined above and a least one pharmaceutically acceptable excipient.

For instance, the composition according to the present invention may contain 0.5-60% by weight of the co-crystal as defined herein and 40-99.5% by weight of one or more pharmaceutically acceptable excipients.

The choice of the excipients will to a large extent depend on factors such as the particular mode of administration, the effect on solubility and stability, and the nature of the dosage form.

Pharmaceutical compositions according to the present invention may be in any form suitable for the application to humans and/or animals, preferably humans including infants, children and adults and can be produced by standard procedures known to those skilled in the art.

The pharmaceutical composition of the present invention preferably is an oral solid composition, such as for instance a capsule, pellet, tablet, cachet, chewable dosage forms, powder: lozenge, granules, oral soluble granulate, suspension, emulsion, spray, or as dry powdered form to be reconstituted with a liquid medium The pharmaceutical composition can additionally contain one or more pharmaceutically acceptable excipients, such as fillers, binders, glidants, disintegrants, flow regulating agents and release agents.

Suitable excipients are for example disclosed in "Handbook of Pharmaceutical Excipients", 3rd Edition, published by A. H. Kibbe, American Pharmaceutical Association, Washington, U.S.A., and Pharmaceutical Press, London.

Suitable fillers are for example lactose (monohydrate, spray-dried monohydrate, anhydrous and the like), mannitol, xylitol, dextrose, sucrose, sorbitol, microcrystalline cellulose, starch, dibasic calcium phosphate dihydrate and calcium hydrogen phosphate.

Fillers can be present in an amount of 0-80% by weight, preferably in an amount of 10-60% by weight of the total weight of the composition.

Suitable binders are for example polyvinylpyrrolidone, microcrystalline cellulose hydroxypropyl cellulose, hydroxypropyl methylcellulose, methylcellulose, hydroxyethyl cellulose, sugars, dextran, cornstarch, gelatin, polyethylene glycol, natural and synthetic gums, pregelatinised starch.

Binders can be present in an amount of 0-80% by weight, preferably in an amount of 10-60% by weight of the total weight of the composition.

Binders are generally used to impart cohesive qualities to a tablet formulation. Suitable glidants are for example alkaline earth metal salts of fatty acids, like stearic acid such as magnesium stearate, calcium stearate, zinc stearate, sodium stearyl fumarate, and mixtures of magnesium stearate with sodium lauryl sulphate.

The glidant can be present for example in an amount of 0-2% by weight, preferably in an amount of 0.5-1.5% by weight of the total weight of the composition.

Suitable disintegrants are for example croscarmellose sodium, sodium carboxymethyl starch, crosslinked polyvinylpyrrolidone (crosspovidone), sodium carboxymethylglycolate, sodium starch glycolate, sodium carboxymethyl cellulose, calcium carboxymethyl cellulose, polyvinylpyrrolidone, methyl cellulose, microcrystalline cellulose, lower alkyl-substituted hydroxypropyl cellulose, starch, pregelatinised starch, sodium alginate and sodium bicarbonate.

The disintegrant can be present in an amount of 0-20% by weight, preferably in an amount of 1-15% by weight of the total weight of the composition.

A suitable flow-regulating agent is for example colloidal silica. The flow regulating agent can be present in an amount of 0-8% by weight, preferably in an amount of 0.1-3% by weight of the total weight of this composition.

A suitable release agent is for example talcum. The release agent can be present in an amount of 0-5% by weight, preferably in an amount of 0.5-3% by weight of the total weight of the composition.

The solid composition may be coated, preferably film coated.

Suitable coating agents are for example cellulose derivatives, poly(meth)acrylate, polyvinyl pyrrolidone, polyvinyl acetate phthalate, and/or shellac or natural rubbers such as carrageenan.

There are many situations in which it will be advantageous or even necessary to deliver the co-crystal of the present invention as a solid, for instance by installing a solid implant composition into suitable body tissues or cavities.

The implant may comprise a matrix of bio-compatible and bioerodible materials in which particles of the co-crystal of the present invention are dispersed, or in which, possibly, globules or isolated cells of a liquid mixture of the present co-crystal are entrapped. Desirably, the matrix will be broken down and completely absorbed by the body. The composition of the matrix is also preferably selected to provide controlled-, sustained-, and/or delayed release of the co-crystal of the present invention over extended periods.

Alternatively, the co-crystal of the invention may be formulated as a solid, semi-solid, or thixotropic liquid for administration as an implanted depot providing modified release of the active compound.

The present composition can be administered topically to the skin or mucosa, that is dermally, epidermally, subepidermally or transdermally.

The present composition can be administered sublingually or via a suppository.

Typical formulations for this purpose include pour-on, spot-on, dip, spray, mousse, shampoo, powder formulation, gels, hydrogels, lotions, creams, ointments, dusting powders, dressings, foams, films, skin patches, wafers, implants, depots, sponges, fibres, bandages, microemulsions, orosoluble granulates. Liposomes may also be used.

The pharmaceutical composition of the present invention may be a solid composition for the extemporaneous preparation of a solution for oral or parenteral administration, to be administered for example by intramuscular, intrapentoneal, or intravenous injection.

The pharmaceutical composition of the present invention can be prepared by methods well known to a person skilled in the art.

The composition of the invention may be of immediate-, delayed-, modified-, sustained-, pulsed- or controlled-release type.

According to a further embodiment, the pharmaceutical composition of the invention may comprise the co-crystal of the invention and at least another pharmaceutically active ingredient.

The other pharmaceutically active ingredient will be determined by the circumstances under which the therapeutic agent of the present invention is administered.

A further object of the present invention is the co-crystal of the invention for use as a medicament.

The medical use can be curative, prophylactic or palliative.

The association of the two active ingredients in the same crystal can exhibit several advantages for the present medical use First, Gabapentin and Ketoprofen Lysine being linked in the co-crystal, often behave as a single chemical entity, thus facilitating the treatments, formulation, dosage etc.

Furthermore the two active ingredients are complementing each other in the treatment especially of pain, but possibly also of various other diseases or symptoms.

Another advantage is that the association of two active ingredients into one unique species may allow for a better Pharmacokinetic/Pharmacodynamic (PKPD) including also a better penetration of the blood-brain barrier, which helps in the treatment of pain.

The co-crystal and the composition of the present invention can show a synergistic activity of the active ingredients Gabapentin and Ketoprofen Lysine.

This synergy provides can provide enhanced clinical efficacy compared to the individual components of the co-crystal when administered separately, or a reduction in the required dose of each compound, leading to a reduction in side effects whilst maintaining or enhancing the clinical effectiveness of the compounds and treatment.

For example, the patient may experience an improved reduction in the frequency and severity of pain and/or inflammation. Furthermore, the patient may benefit from a longer duration of action from the co-crystal treatment than from treatment with Gabapentin or with Ketoprofen Lysine or with their combination.

It is necessary for the skilled artisan, such as a physician or a veterinarian, not only to determine the preferred route of administration and the corresponding dosage form and amount, but said artisan must also determine the dosing regimen.

The daily dosage for humans and animals may vary depending on factors that have their basis in the respective species or other factors, such as age, sex, weight or degree of illness and so forth.

The daily dosage of the co-crystal according to the invention for humans preferably provides for Ketoprofen acid form in an amount between 25 and 200 mg, preferably between 25 and 100 mg, more preferably of about 50 mg, from 1 to 6 times per day, preferably from 1 to 4 times a day, resulting the total Gabapentin amount very low if compared to the normal dosage of Gabapentin alone.

A further object of the present invention is the co-crystal of the invention for use in the treatment of pain and/or inflammation.

The co-crystal and the composition of the present invention are preferably used for the treatment of pain, preferably of acute or chronic pain and inflammation, preferably neuroinflammation.

Preferably, said pain is selected from headache, toothache, menstrual pain, muscle pain, neuropathic pain, diabetic, neuropathy, pain associated to neuroinflammation, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

A further object of the present invention is a method for the treatment of pain and/or inflammation comprising administering to a patient an effective amount of the co-crystal of the invention.

Experimental Part

In the following, the manufacture of the co-crystal of Ketoprofen, Lysine and Gabapentin, its analytical and biological characterization are described

1. Synthesis of the 1:1:2 Ketoprofen-Lysine-Gabapentin Co-Crystal

Ketoprofen Lysine co-crystal Form I (3.0 g, 1.0 eq.), prepared as described in the European Patent Application n. EP18215336.1 or in the International Patent Application PCT/EP2019/025464 and Gabapentin (2.56 g, 2.0 eq.) were dissolved in 60 ml of boiling methanol. The clear solution was allowed to cool at room temperature, polish-filtered (0.45 μm HPLC filter) and then added to 240 ml of THF under stirring. The solid precipitation took place in approximatively 45 minutes and the suspension was stirred at 25° C. for 2 hours (300 rpm), The solid product was isolated by vacuum filtration on a paper filter, washed with methanol (2×3 ml) and then squeezed under a nitrogen flow for approximatively 10 minutes. The solid was gently ground and then dried at 40° C. and 30 mbar overnight affording 4.8 grams of the desired product as a white solid (Yield: 86%).

2. XRPD Analysis

The XRPD analysis was carried out with the following instrument and under the conditions reported in Table 1 below:

TABLE 1

| Instrument type: | Rigaku MiniFlex600 |
| --- | --- |
| Application SW: | Miniflex Guidance |
| Measurement Details | |
| Measurement type: | Single scan |
| Sample mode: | Reflection |
| Scan | |
| Scan range: | 3.000-40.000° (2θ) |
| Step size: | 0.01° (2θ) |
| Speed: | 10.0°/min (2θ) |
| Scan mode: | Continuous |
| Used wavelength | |
| Intended wavelength type: | Kα1 |
| Kα1: | 1.540598 Å |
| Kα2: | 1.544426 Å |
| Kα2/Kα1 intensity ratio: | 0.50 |
| Kα: | 1.541874 Å |
| Kα: | 1.392250 Å |
| Instrument Details | |
| X-Ray Generator | |
| Tube output voltage: | 40 kV |
| Tube output: | 15 mA |
| High-voltage generation method: | High-frequency Cockcroft-Walton method |
| Stability: | Within ±0.05% for both the tube voltage and tube current, with reference to ±10% of input power variation. |
| X-ray tube | |
| Name: | Toshiba Analix type A-26L |
| Anode material: | Cu |
| Maximus output: | 0.60 kW |

TABLE 1-continued

| Focus size: | 1 × 10 mm |
| --- | --- |
| Kβ Filter | |
| Name: | Ni-filter |
| Thickness (mm): | 0.015 |
| Material: | Ni |
| Goniometer (Angle measuring device) | |
| Type: | Vertical θ/2θ |
| Goniometer radius: | 150 mm |
| Scanning axis: | θ/2θ linked |
| 2θ scanning range: | +2° to +140° |
| θ/2θ axis minimum step angle: | 0.005° (2θ) |
| Position speed: | 500°/min (2θ) |
| Scanning speed: | 0.01 to 100°/min |
| Datum angle: | 2θ = 10° |
| X-ray take-off angle: | 6° (fixed) |
| Slit | |
| DS: | 1.25° |
| IHS: | 10.0 mm |
| SS: | none (open) |
| RS: | none (open) |
| Incident side Soller slit: | 2.5° |
| Receiving side Soller slit: | 2.5° |
| Detector | |
| Name: | D/tex Ultra High-speed 1D Detector |
| Window material: | Be |
| Effective window size: | 13 mm (H) × 20 mm (W) |
| Dimensions: | 80 mm (L) |

Figure 2:
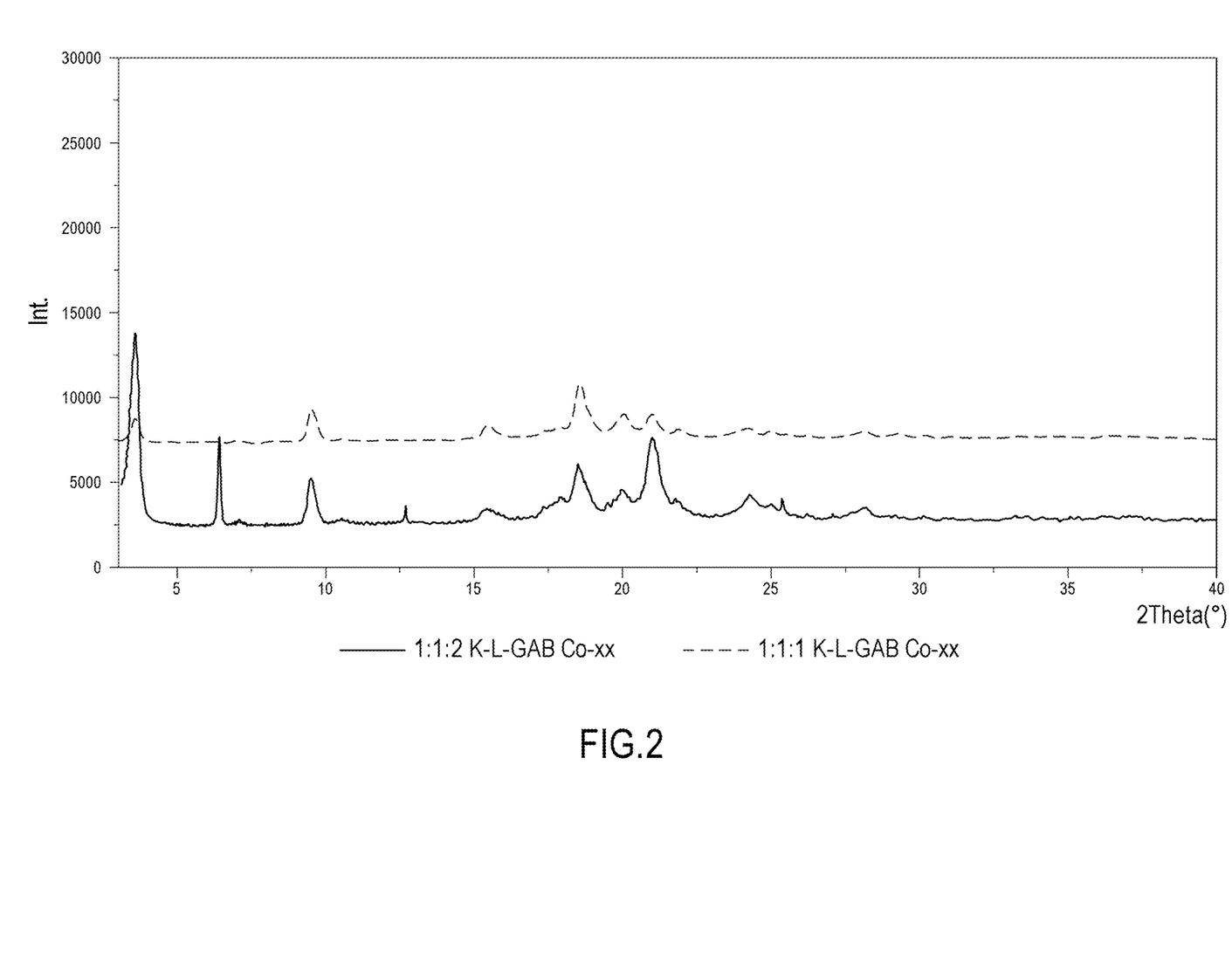
FIG. 2: Powder X-Ray diffraction patterns of 1:1:2 Ketoprofen-Lysine-Gabapentin co-crystal and 1:1:1 Ketoprofen-Lysine-Gabapentin co-crystal

The Powder X-Ray diffractogram of 1:1:2 Ketoprofen-Lysine-Gabapentin co-crystal is reported in FIG. 1. A comparison between the Powder X-Ray diffractograms of Ketoprofen-Lysine-Gabapentin co-crystals 1:1:1 and 1:1:2 is reported in FIG. 2. The XRPD peak list of the 1:1:2 Ketoprofen-Lysine-Gabapentin co-crystal is reported in Table 2 below:

TABLE 2

XRPD Peak Least 1:1:2 Ketoprofen-Lysine-Gabapentin co-crystal

| Pos. [°2Th.] | Height [cts] | FWHM [°2Th.] | d-spacing [Å] | Rel. Int. [%] |
| --- | --- | --- | --- | --- |
| 3.6251 | 11156.56 | 0.0984 | 3.04710 | 100.00 |
| 6.2531 | 5100.16 | 0.3542 | 2.96523 | 45.71 |
| 9.5963 | 2389.96 | 0.3149 | 2.17056 | 21.42 |
| 10.2396 | 71.53 | 0.2574 | 4.99385 | 0.64 |
| 12.6123 | 720.19 | 0.1362 | 4.79862 | 6.46 |
| 15.8941 | 741.78 | 0.3442 | 4.43123 | 6.65 |
| 17.1933 | 961.40 | 0.1481 | 4.22708 | 8.62 |
| 17.2258 | 742.52 | 0.1755 | 4.07409 | 6.66 |
| 18.6398 | 2923.12 | 0.4700 | 3.67121 | 26.20 |
| 20.4830 | 1912.02 | 0.3149 | 3.51106 | 17.14 |
| 21.6611 | 4299.12 | 0.3287 | 3.18062 | 38.53 |
| 21.9123 | 621.98 | 0.2123 | 3.30203 | 5.58 |
| 24.5267 | 913.23 | 0.2311 | 3.16223 | 8.19 |
| 24.8963 | 617.47 | 0.0984 | 3.04704 | 5.53 |
| 25.0002 | 615.02 | 0.3542 | 2.96564 | 5.51 |
| 26.3078 | 45.19 | 0.1782 | 2.87075 | 0.41 |
| 28.0023 | 311.23 | 0.2358 | 4.99385 | 2.79 |
| 29.2987 | 105.42 | 0.5399 | 3.48072 | 0.94 |
| 30.0023 | 107.36 | 0.3002 | 3.38773 | 0.96 |
| 31.1012 | 64.31 | 0.3912 | 3.16223 | 0.58 |

3. Thermal Analyses

DSC Analysis

The analysis was carried out using the instrument DSC Mettler Toledo DSC1.

The sample was weighed in an aluminum pan hermetically sealed with an aluminum cover. The analysis was performed by heating the sample from 25° C. to 320° C. at 10 K/min, under the conditions shown in Table 3 below:

TABLE 3

| Temperature Data | |
|---|---|
| Temperature range | −40° C. to 450° C. |
| Temperature accuracy | ±0.2K |
| Temperature precision | ±0.02K |
| Furnace temperature resolution | ±0.00006K |
| Heating rate | 0.02 to 300K/min |
| Cooling rate | 0.02 to 50K/min |
| Cooling time | 5 min (100° C. to 0° C.) |
| Calorimetric Data | |
| Sensor type | FRS5 |
| Sensor material | Ceramic |
| Number of thermocouples | 56 |
| Signal time constant | 1.8 s |
| Indium peak (height to width) | 17 |
| TAWN resolution | 0.12 |
| Sensitivity | 11.9 |
| Resolution | 0.04 μW |
| Digital resolution | 16.8 million points |

The analysis was carried out on a sample of 1:1:2 Ketoprofen-Lysine-Gabapentin co-crystal. The DSC thermogram is shown in FIG. 3.

Figure 4:
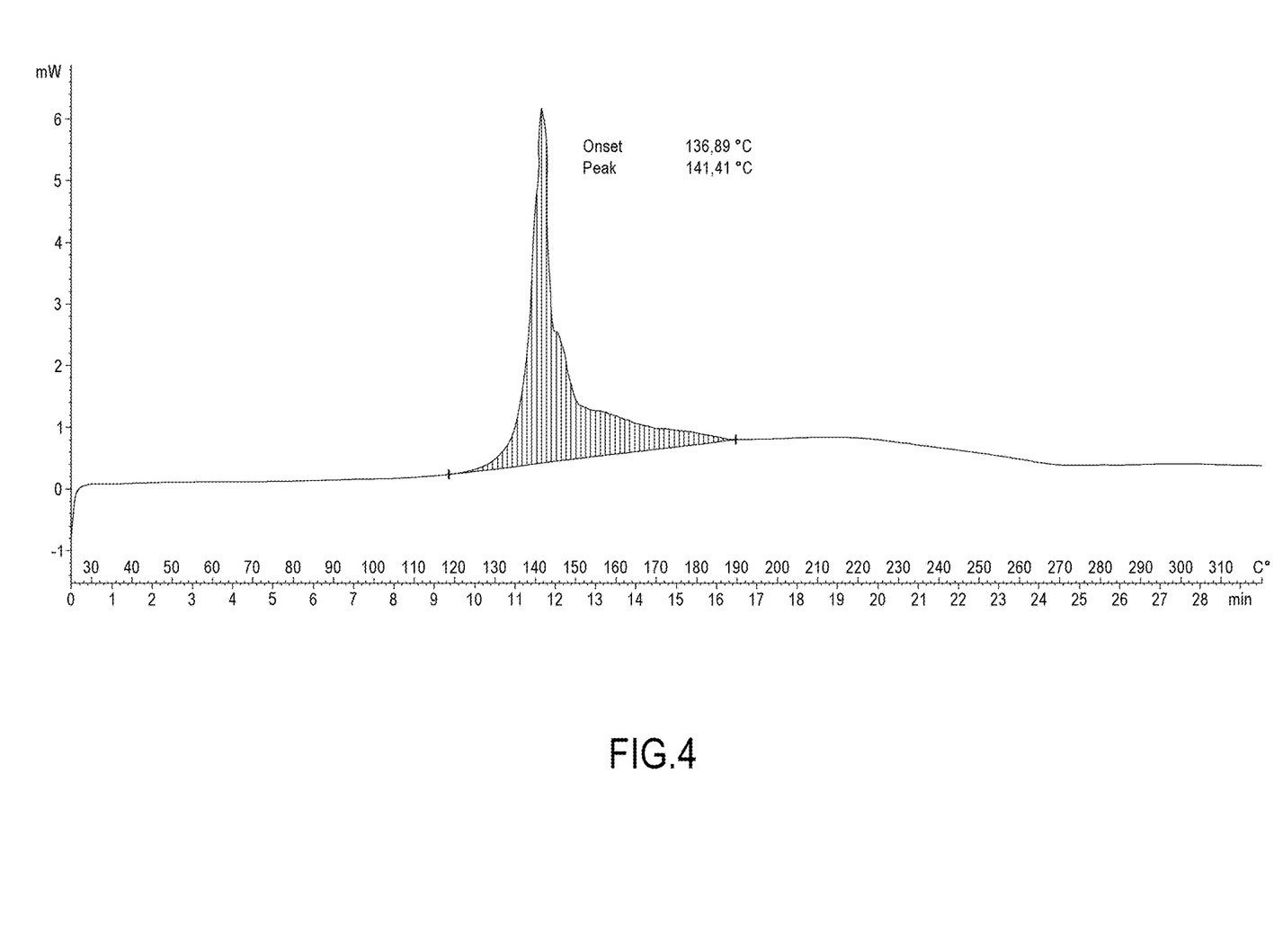
FIG. 4: DSC thermogram of 1:1:1 Ketoprofen-Lysine-Gabapentin co-crystal
Figure 5:
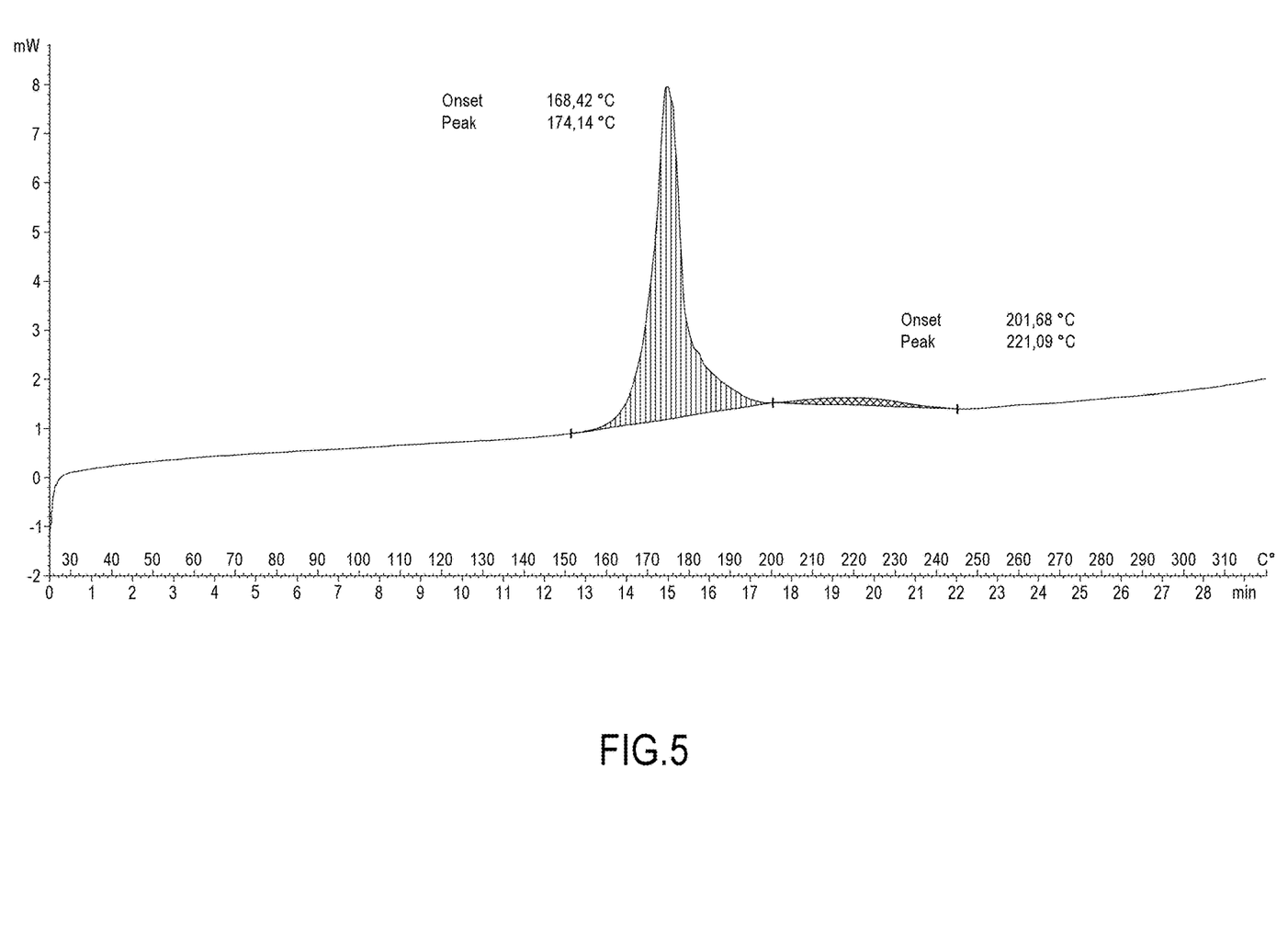
FIG. 5: DSC thermogram of Ketoprofen Lysine co-crystal Form I
Figure 6:
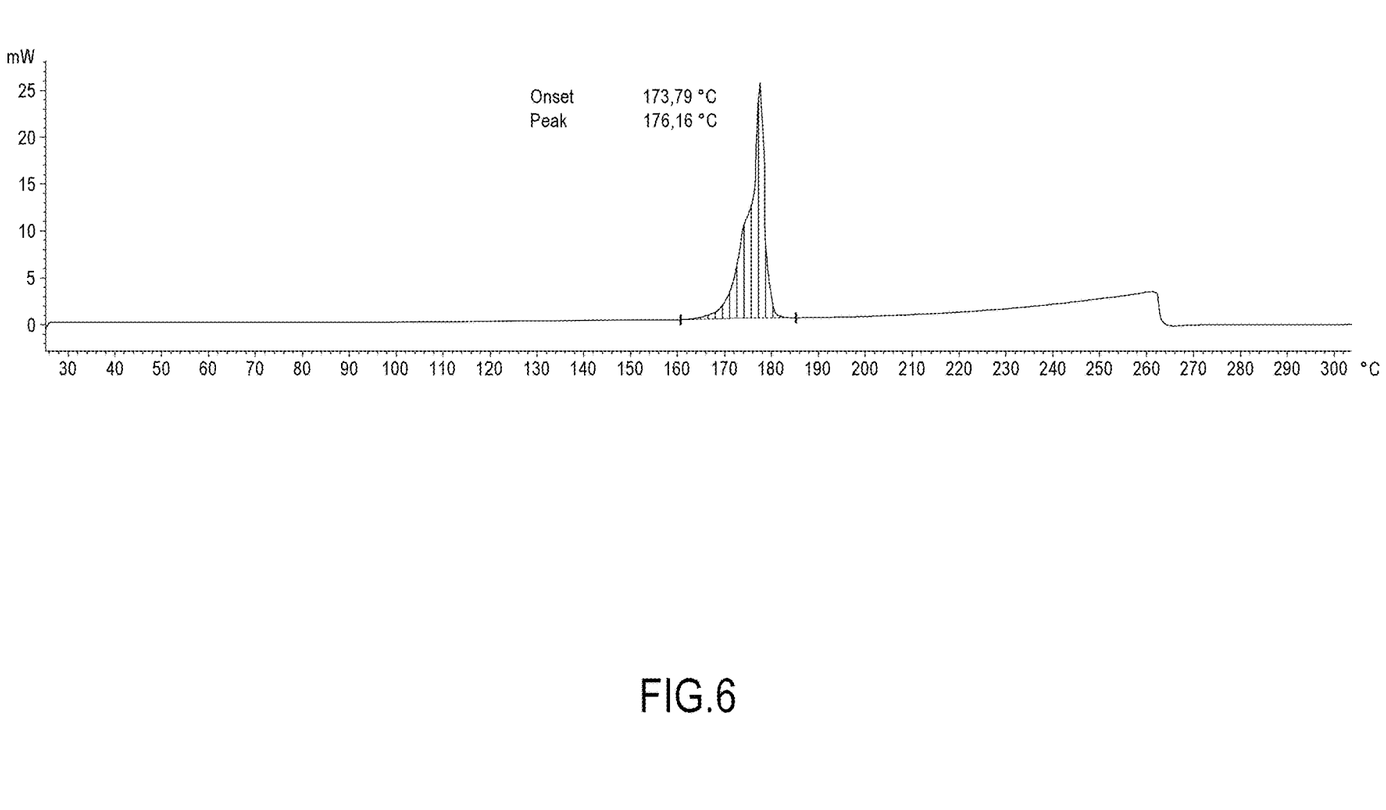
FIG. 6: DSC thermogram of Gabapentin

In FIGS. 4, 5 and 6 the thermograms of 1:1:1 Ketoprofen-Lysine-Gabapentin co-crystal, of Ketoprofen Lysine co-crystal Form I and of Gabapentin are respectively reported.

The DSC thermogram of FIG. 3 showed a single endothermic event at 143.55° C. (onset 139.57° C.), associated to sample melting and degradation. This peak was clearly different from the endothermic peaks of the thermograms of 1:1:1 Ketoprofen-Lysine-Gabapentin co-crystal, of Ketoprofen Lysine co-crystal Form I and of Gabapentin shown in FIGS. 4 to 6.

4. Liquid and Solid State NMR

$^1$H-Nuclear magnetic resonance (NMR) spectra were recorded in the indicated solvent with tetramethylsilane (TMS) as internal standard on a Bruker Avance3 400 MHz instrument. Chemical shifts are reported in parts per million (ppm) relative to the internal standard. Abbreviations are used as follows: s=singlet, d=doublet, t=triplet, q=quartet, m=multiplet, dd=doublets of doublet, br=broad. Coupling constants (J values) are given in hertz (Hz).

The solid-state $^{13}$C CPMAS spectra of 1:1:2 Ketoprofen-Lysine-Gabapentin co-crystal and pure Gabapentin were acquired with a Jeol ECZR 600 instrument, operating at 600.17 and 150.91 MHz, respectively for $^1$H and $^{13}$C nuclei. The powder samples were packed into a cylindrical zirconia rotor with a 3.2 mm o.d. and a 60 μl volume. A sample was collected from each batch and used without further preparations to fill the rotor. The $^{13}$C CPMAS spectra were acquired at room temperature, at a spinning speed of 20 kHz, using a ramp cross-polarization pulse sequence with a 90° $^1$H pulse of 2.1 μs and a contact time of 3.5 ms. An optimized recycle delay of 5.7 (Ketoprofen-Lysine-Gabapentin) or 100 s (GAB) was used, for a number of scans of 2200 (Ketoprofen-Lysine-Gabapentin) or 20 (Gabapentin). For every spectrum, a two-pulse phase modulation (TPPM) decoupling scheme was used, with a radiofrequency field of 108.5 kHz. The $^{13}$C chemical shift scale was calibrated through the methylene signal of external standard glycine (at 43.7 ppm). As for the $^{13}$C T$_1$-$^1$H analysis, 12 spectra were acquired for 350 scans with different relaxation delays, included in the range 0.1-60 s and calculated by the Delta v5.2.1 software through an exponential algorithm. The spectra were acquired at a spinning speed of 20 kHz at room temperature using a ramp cross-polarization pulse sequence with a 90° $^1$H pulse of 2.1 μs and a contact time of 2 ms.

$^1$H-NMR Spectra of 1:1:2 Ketoprofen-Lysine-Gabapentin Co-Crystal $^1$H-NMR spectrum of Ketoprofen-Lysine-Gabapentin co-crystal confirmed the concomitant presence in the sample of Ketoprofen-Lysine-Gabapentin with 1:1:2 stoichiometry.

The multiplicity and the assignment of the signals in line with the atoms numbering shown in Scheme 1

Scheme 1

Ketoprofen

Lysine

Gabapentin are reported in Table 4 below:

TABLE 4

| $^1$H-NMR (Ratio KET:LYS:GAB 1:1:2) | | |
|---|---|---|
| δ ppm | Multiplicity | Assignment |
| 7.75-7.78 | m, 2H | Ar KET |
| 7.69-7.72 | m, 2H | Ar KET |
| 7.60-7.62 | m, 2H | Ar KET |
| 7.48-7.56 | m, 3H | Ar KET |
| 3.71 | t, J = 6.4 Hz, 1H | CH (2') LYS |
| 3.69 | quart., J = 7.2 Hz, 1H | CH (2) KET |
| 2.96 | t, J = 7.6 Hz, 2H | CH$_2$ (6') LYS |
| 2.95 | s, 4H | CH$_2$ (9") GAB |
| 2.36 | s, 4H | CH$_2$ (2") GAB |
| 1.79-1.85 | m, 2H | CH$_2$ (5') LYS |
| 1.62 | quint., J = 7.6 Hz, 2H | CH$_2$ (3') LYS |
| 1.41 | d, J = 7.2 Hz, 3H | CH3 (3) KET |
| 1.29-1.52 | m, 22H | CH$_2$ (4",5",6",7",8") GAB; CH$_2$ (4') LYS |

The $^1$H-NMR spectrum (400 MHz, D$_2$O) of 1:1:2 Ketoprofen-Lysine-Gabapentin co-crystal is shown in FIG. 7.

Solid State $^{13}$C CPMAS Spectra of 1:1:2 Ketoprofen-Lysine-Gabapentin Co-Crystal A new homogeneous phase of Ketoprofen-Lysine-Gabapentin was confirmed by $^{13}$C-CPMAS spectra. The stoichiometry was assessed to be 1:1:2, with one independent molecule of Ketoprofen, Lysine and two of Gabapentin in the unit cell. Ketoprofen carboxylic group is deprotonated and interacts with protonated Lysine ε-NH$_3^+$ group through ionic bonds forming a neutral salt. The Ketoprofen Lysine neutral salt interacts with two molecules of Gabapentin through non-ionic bonds forming a co-crystal. Both Lysine and Gabapentin are in a zwitterionic state in the new crystal form.

In Table 5 below the characteristic solid-state $^{13}$C-NMR resonances are summarized:

TABLE 5 solid state $^{13}$C-NMR

| $^{13}$C δ (ppm) | Assignment |
|---|---|
| 194.5 | 10 |
| 181.4 | 1 |
| 178.9 | 1' |
| 178.7 | 1" |
| 178.1 | 1" |
| 145.9 | Aromatic C$_q$ |
| 139.6 | Aromatic C$_q$ |
| 136.2 | Aromatic C$_q$ |
| 135.5 | Aromatic CH |
| 132.9 | Aromatic CH |
| 131.2 | Aromatic CH |
| 130.2 | 3 Aromatic CH |
| 127.8 | 2 Aromatic CH |
| 125.2 | Aromatic CH |
| 54.1 | 2' |
| 49.8 | 9" |
| 48.3 | 2 |
| 42.5 | 6' |
| 37.1 | 2" + 4" or 8" |
| 36.8 | 3' + 4" or 8" |
| 34.6 | 6" |
| 30.1 | 5' + 3" |
| 26.1 | 4' |
| 25.2 | 3 |
| 23.1 | 5" or 7" |
| 21.1 | 5" or 7" |

FIG. 8 displays the CPMAS NMR spectra of 1:1:2 Ketoprofen-Lysine-Gabapentin co-crystal.

All signals in the spectrum of Ketoprofen-Lysine-Gabapentin co-crystal are characterized by similar $^1$H T$_1$ values (around 6.5 s), meaning that spin diffusion is active among the molecules of Ketoprofen, Lysine and Gabapentin, i.e. the four molecules are in the same unit cell.

Four distinct resonances for carboxylic/carboxylate groups were observed at 181-178 ppm, suggesting a 1:1:2 stoichiometric ratio for the Ketoprofen-Lysine-Gabapentin system.

The two molecules of Gabapentin are zwitterions: their carboxylate groups are in deprotonated form in 1:1:2 Ketoprofen-Lysine-Gabapentin at 1781 and 178.1 ppm. The zwitterionic carboxylate of Lysine is at 178.9 ppm in 1:1:2 Ketoprofen-Lysine-Gabapentin, due to the involvement of the carboxylate group in strong hydrogen bonds. The Lysine is supposed to be in the zwitterionic form.

Finally, the carboxylic group of Ketoprofen in 1:1:2 Ketoprofen-Lysine-Gabapentin is at 181.4 ppm.

The invention claimed is:

1. A co-crystal of Ketoprofen, Lysine and Gabapentin, wherein the molar ratio of the components is 1:1:2.

2. The co-crystal according to claim 1, characterized by the following XRPD diffraction peaks: 3.6, 6.3, 18.6 and 21.7 degrees 2-theta±0.2 degrees 2-theta.

3. The co-crystal according to claim 2, further characterized by the following XRPD diffraction peaks: 9.6, 17.2 and 20.5 degrees 2-theta±0.2 degrees 2-theta.

4. The co-crystal according to claim 1, further characterized by one or more of the following:
 a DSC thermogram with the endothermic peak corresponding to the melting point at about 143.5° C. as shown in FIG. 3,
 solution $^1$H-NMR signals shown in FIG. 7, and
 solid state $^{13}$C CPMAS signals as shown in FIG. 8.

5. The co-crystal according to claim 1, wherein the Ketoprofen is (S)-Ketoprofen and/or the Lysine is(S)-Lysine.

6. A method for the prevention, reduction or treatment of pain and/or inflammation in a subject in need thereof, comprising administration of the co-crystal according to claim 1, alone or in combination with one or more pharmaceutically acceptable excipients.

7. The method according to claim 6, wherein the pain is acute or chronic pain.

8. The method according to claim 6, wherein the pain is selected from headache, toothache, menstrual pain, muscle pain, neuropathic pain, pain associated to neuroinflammation, diabetic neuropathy, cancer pain, osteoarthritis, low back pain, sciatalgia, fibromyalgia, trigeminal neuralgia; post-surgical and post-operative pain, post herpetic neuralgia, rheumatoid arthritis, ankylosing spondylitis, frozen shoulder, phantom limb pain or HIV pain.

9. A pharmaceutical composition comprising the co-crystal according to claim 1 and a least one pharmaceutically acceptable excipient.

10. The pharmaceutical composition according to claim 9, which contains 0.5-60% by weight of the co-crystal and 40-99.5% by weight of one or more pharmaceutically acceptable excipients.

11. The pharmaceutical composition according to claim 9, which is a solid composition for oral administration.

12. The pharmaceutical composition according to claim 10, which is a solid composition for oral administration.

13. A process for the preparation of the co-crystal according to claim 1, which comprises:
 a) suspending Ketoprofen, Lysine and Gabapentin, in a molar ratio of 1/1 to 1.5/2 to 2.5, in a suitable solvent,
 b) dissolving Ketoprofen, Lysine and Gabapentin, optionally by heating the suspension and/or under stirring, till a clear solution is obtained
 c) subsequently cooling the solution, and
 d) optionally adding an anti-solvent.

14. The process according to claim 13, wherein the Ketoprofen and Lysine in step a) are in form of a Ketoprofen Lysine salt or a co-crystal.

15. The process according to claim 13, wherein the Ketoprofen is the free acid and/or the Lysine is in neutral form.

16. The process according to claim 13, wherein the Gabapentin is in neutral form (zwitterionic internal salt).

17. The process according to claim 13, wherein in step a) the molar ratio of Gabapentin vs Ketoprofen is between 2:1 and 2.2:1.

18. The process according to claim 17, wherein in step a) the molar ratio of Gabapentin vs Ketoprofen is about 2:1.

* * * * *